United States Patent
Pronovost et al.

(10) Patent No.: US 7,432,679 B2
(45) Date of Patent: Oct. 7, 2008

(54) NON-INTRUSIVE METHOD FOR EXTRAPOLATING AN INTERNAL STATOR TEMPERATURE

(75) Inventors: Jean Pronovost, Saint-Mathleu-de-Beloell (CA); Marius Cloutier, Longueuli (CA); Marc Bissonnette, Boucherville (CA); Louis-Pierre Lalonde, Varennes (CA)

(73) Assignee: Vibrosystm Inc., Longueuil, Quebec (CA)

( * ) Notice: Subject to any disclaimer, the term of this patent is extended or adjusted under 35 U.S.C. 154(b) by 25 days.

(21) Appl. No.: 11/576,764

(22) PCT Filed: Oct. 12, 2005

(86) PCT No.: PCT/CA2005/001581

§ 371 (c)(1),
(2), (4) Date: Apr. 5, 2007

(87) PCT Pub. No.: WO2006/039808

PCT Pub. Date: Apr. 20, 2006

(65) Prior Publication Data

US 2008/0067963 A1     Mar. 20, 2008

Related U.S. Application Data

(60) Provisional application No. 60/617,063, filed on Oct. 12, 2004.

(51) Int. Cl.
*G01K 13/04* (2006.01)
*G01R 31/34* (2006.01)
*G05D 23/00* (2006.01)

(52) U.S. Cl. .......... 318/471; 318/473; 374/134; 374/135; 374/E13.01; 374/E13.08

(58) Field of Classification Search .......... 174/134, 174/135, E13.01; 73/862, 623, 54, 35; 318/471, 318/473; 310/68 C; 340/584
See application file for complete search history.

(56) References Cited

U.S. PATENT DOCUMENTS

| | | | |
|---|---|---|---|
| 4,245,500 A | 1/1981 | Malang | |
| 4,978,230 A * | 12/1990 | Adiutori et al. | 374/43 |
| 5,735,604 A | 4/1998 | Ewals et al. | |
| 5,816,706 A | 10/1998 | Heikkila et al. | |
| 6,517,241 B1 | 2/2003 | Sanderson | |
| 6,534,942 B2 * | 3/2003 | Schmidhuber | 318/563 |
| 6,903,525 B2 * | 6/2005 | Carson et al. | 318/471 |
| 6,945,691 B2 | 9/2005 | Trapasso et al. | |
| 7,311,264 B2 * | 12/2007 | Franke et al. | 374/30 |
| 2006/0164746 A1 * | 7/2006 | Son et al. | 360/69 |
| 2008/0037164 A1 * | 2/2008 | Oh et al. | 360/99.08 |

FOREIGN PATENT DOCUMENTS

JP     2006094576 A   *   4/2006

* cited by examiner

*Primary Examiner*—Lincoln Donovan
*Assistant Examiner*—Eduardo Colon-Santana
(74) *Attorney, Agent, or Firm*—Ogilvy Renault, LLP

(57) ABSTRACT

A method for non-intrusive determination of an internal temperature of a given area of an electrical machine stator, comprises obtaining a temperature gradient between an internal wall of the stator and an external wall of the stator, obtaining temperature measurements at locations on the external wall of the stator, and using the temperature gradient and the external temperature measurements to extrapolate corresponding internal temperatures of the stator.

13 Claims, 9 Drawing Sheets

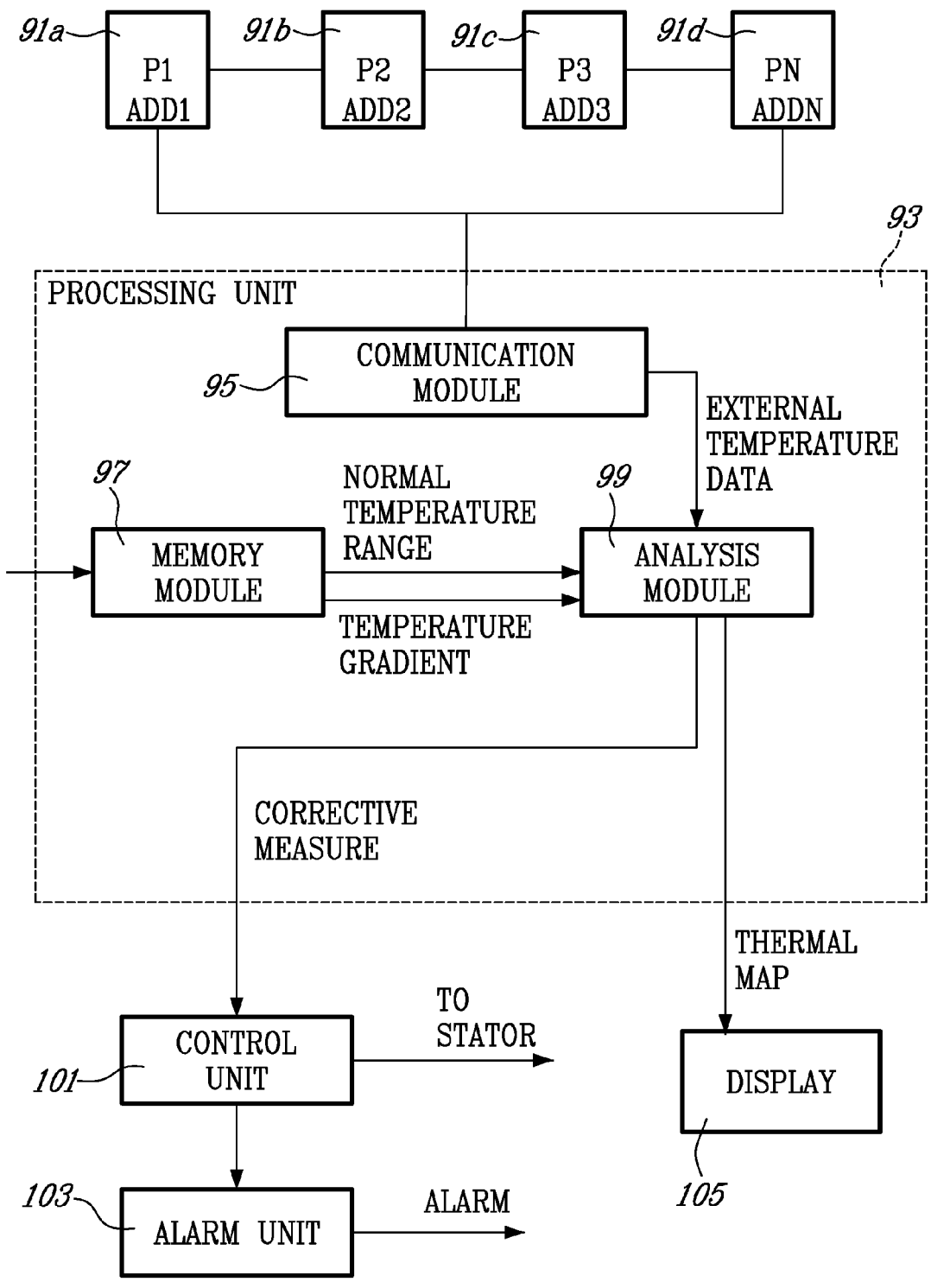

NON-INTRUSIVE METHOD FOR EXTRAPOLATING AN INTERNAL STATOR TEMPERATURE

CROSS-REFERENCE TO RELATED APPLICATIONS

This application is a national phase entry of PCT patent application number PCT/CA2005/001581 filed Oct. 12, 2005 which claims priority of U.S. Provisional Patent Application Ser. No. 60/617,063 filed on Oct. 12, 2004, the contents of both of which are hereby incorporated by reference.

TECHNICAL FIELD

This application relates to stator bars. More specifically, it relates to the field of stator bar defect detection.

BACKGROUND OF THE INVENTION

Several problems have been associated to the operation of stators of rotating machines, the effects of which can be detrimental to their yield and operating life. The most important problems have been identified to be: the gathering of deposits that obstruct cooling ducts of stator bars, the loss of insulation between elementary conductors (stator winding) that constitute a stator bar, the loss of quality of the connections of stator bars, and the loss of insulation of stator laminations.

Detection of defects, such as obstructive deposits in a cooling duct of a stator bar, may however be problematic. The liquid circulation cooling system plays a crucial role in the life span of rotating machines. An obstruction, even a very small one, of the cavities of the stator bars causes a considerable elevation of temperature, because the electrical current that circulates therein is very high. A large amount of thermal energy must then be dissipated by the stator bar. The quantity of heat to be dissipated in the stator bar is proportional to the square of the current that circulates therein and is given by the following relationship:

$$P_b \alpha I^2 \times R \qquad (1)$$

where
$P_b$=Heating load to be dissipated by the stator bar (Watts)
I=Current(Amperes)
R=Ohmic Resistance of stator bar (Ohms)

To allow heat to be dissipated, cavities inside of which a liquid circulates are provided in the heart of each stator bar.

Heat transfer between the liquid and a radiator allows heat to be evacuated.

One of the major problems with machines that are cooled by liquid circulation is the accumulation of a deposit on the internal walls of these cavities. This undesirable situation causes a decrease of liquid flow, causing the temperature of the stator bar to increase even more, which can lead to a machine breakdown as a result of a destruction of the insulating material.

Another problem associated with the operation of rotating machines having stator bars is the loss of insulation between conductors (for example: Roëbel bars) of the stator bar.

Each stator bar is made of a plurality of conductors that are insulated from one another (multicore cables) to decrease skin effects. Skin (or pellicular) effects result from an electrical current that does not circulate uniformly in a cross-section of a conductor, but rather on its peripheral portion. Segmentation of a stator bar into a plurality of conductors has the effect of increasing the effective cross-section of the stator bar and, by the same token, decreasing the resistance of the conductor.

Subdividing a stator bar into a plurality of insulated conductors, as seen in FIG. 2, allows for a decrease of skin effects. However this decrease is directly related to the good operating conditions of the insulations. If the insulant becomes deteriorated, there is an increase of skin effects, as well as an increase in electrical resistance and temperature. This loss of insulation takes place mainly at the extremities of stator bars because of the possible movement produced by a leverage effect.

Yet another problem associated to the operation of stator bars is the loss in quality of the connections between stator bars. Stator bars are connected to one another through silver welds. Any deterioration of a connection causes a decrease in machine efficiency. A deteriorated connection point causes an increase of the resistance of the conductor, yielding a temperature increase at the deteriorated site.

Finally, loss of insulation in stator laminations is another problem associated with stator bar operation. The stator nucleus of a machine is made of piles of sheet iron plates that are separated from one another by means of an insulating material. Such an assembly allows for reducing to an acceptable level Foucault currents that are induced by the intense magnetic field generated by the poles of the rotor. If the insulation material is lost in some places, the Foucault currents will intensify in the degraded zone and the local temperature will increase. Such a temperature increase will be harmful to the performance of the machine and may even cause a breakdown following the metal melting.

Whenever one of the above-mentioned problems occurs, the local temperature inside the stator rises at the defective sites. A solution suggested in order to detect the above-mentioned problems has been the mounting, inside the stator, of a large number of temperature probes capable of producing a thermal mapping that covers the whole of the inside of the stator. Such a thermal mapping would allow to determine the probable cause of a defect by detecting an abnormal temperature rise at one or more given points of the thermal cover.

Unfortunately such a theoretical solution is difficult to implement in an actual stator bar environment. It is well-known that strong currents are induced by the elevated currents and the electromagnetic fields that circulate in stator bars. Therefore, the number of temperature probes inside a stator will be limited by the fact that care must taken with respect to the wiring of these probes. Furthermore, the amount of wiring that is required could constitute a safety hazard for the machine operators, as well as hinder the good operation of the machine itself.

While a limited number of such temperature probes may be installed at manufacturing time, the later addition of even a single probe requires major works at a prohibitive cost. For example, such additions would involve the opening of the stator and could, in certain cases, have the added undesirable effect of cancellation of the manufacturer warranty.

There exists therefore a need for a system and method allowing to detect a local elevation of temperature representative of stator defects in a cost-effective manner.

There exists furthermore a need for a system and method allowing early detection of stator defects in a non-intrusive manner so that corrective measures may be administered.

SUMMARY OF THE INVENTION

The proposed system makes it possible to measure and diagnose all of the above-identified problems in an exhaustive manner, by means of a plurality of distributed probes. This system is possible by reason of the restricted quantity of wiring and material that is required to put it into operation at an acceptable cost.

The system gives users reassurance as to the good operation of the machine and allows for monitoring its good operation over time and while the system is in operation. This continuous monitoring allows users to make an intervention at the appropriate moment, thereby limiting important and costly damages. The machine profits from a better yield, and the safety of people is thereby increased.

As seen in FIG. 1, it then becomes conceivable to install at least one probe on each of the stator bars of a machine and thus to detect an obstruction in a cavity of each of the stator bars of the machine, and to detect a deterioration of the insulation between the conductors of a stator bar by measuring its temperature when the machine is in operation. This detection is designed for a machine in normal operation.

According to a first broad aspect of the present invention there is provided a method for non-intrusive determination of an internal temperature of a given area of an electrical machine stator, comprising: obtaining a temperature gradient between an internal wall of the stator and an external wall of the stator; obtaining temperature measurements at locations on the external wall of the stator; and using the temperature gradient and the external temperature measurements to extrapolate corresponding internal temperatures of the stator.

According to another broad aspect of the present invention, there is provided a system for non-intrusive determination of the internal temperature of a given area of an electrical machine stator, comprising: a plurality of temperature probes to be installed on an external wall of the electrical machine stator for measuring an external temperature thereof; a processing unit, including a memory unit for storing a gradient temperature, an analysis module for receiving the external temperature data and calculating, using the temperature gradient, the internal temperatures; and a communication module for receiving the external temperature data from the plurality of temperature probes.

BRIEF DESCRIPTION OF THE DRAWINGS

Further features and advantages of the present invention will become apparent from the following detailed description, taken in combination with the appended drawings, in which:

FIG. 9 is a block diagram of a system for non-intrusive determination of an internal temperature of a given area of an electrical machine stator according to the present invention.

DESCRIPTION OF THE PREFERRED EMBODIMENT

Figure 1:
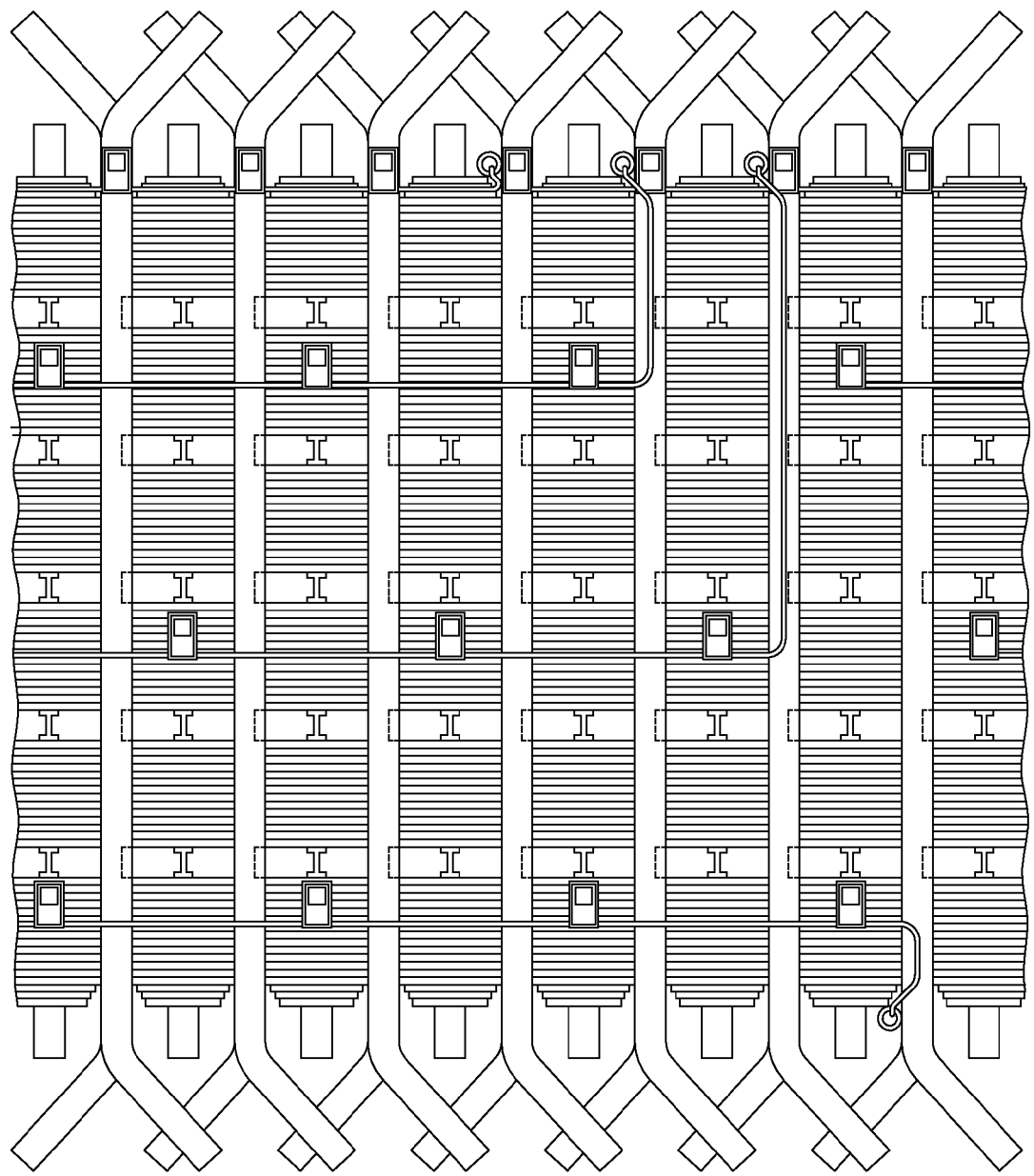
FIG. 1 is a schematic illustration showing localization of probes on an external wall of a stator according to an embodiment of the present invention.
Figure 2:
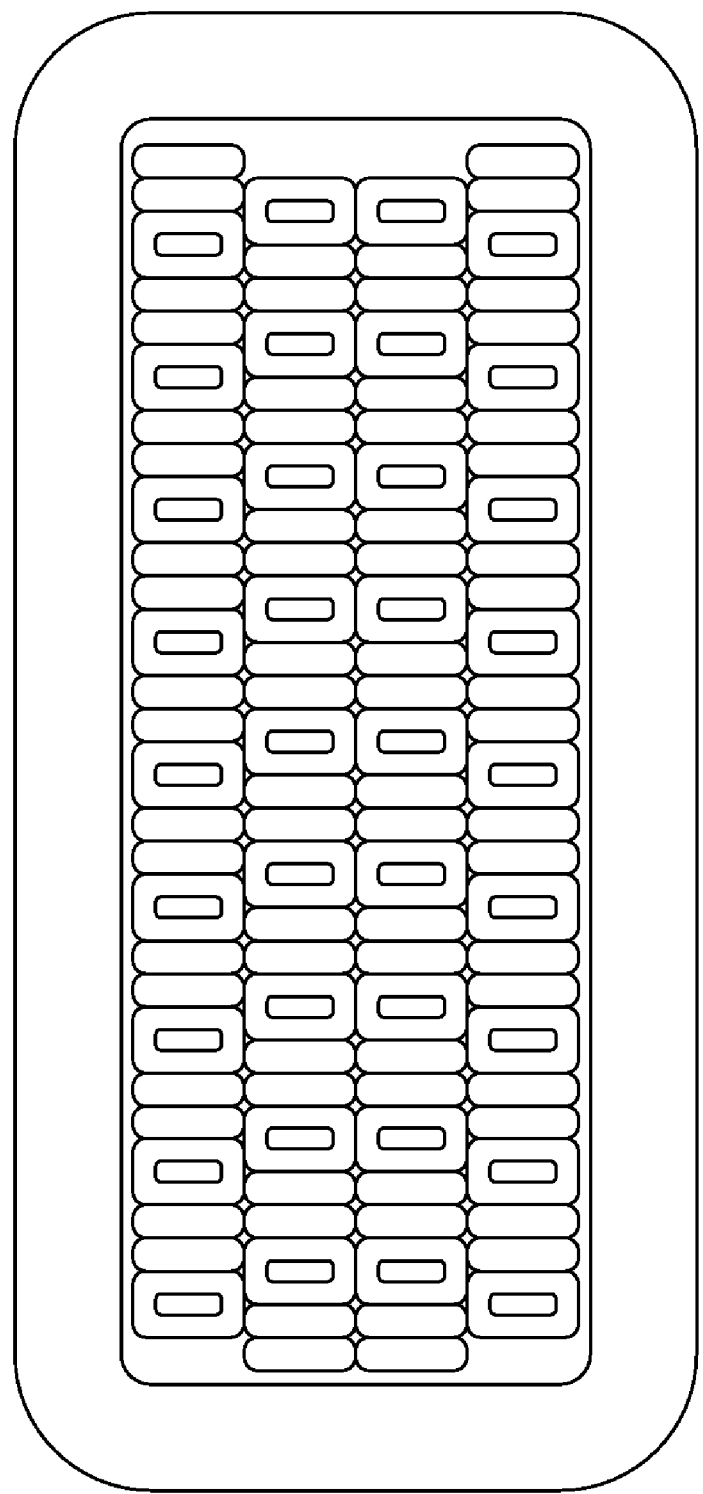
FIG. 2 is a schematic illustration of a stator bar with insulated conductors according to the prior art.
Figure 3:
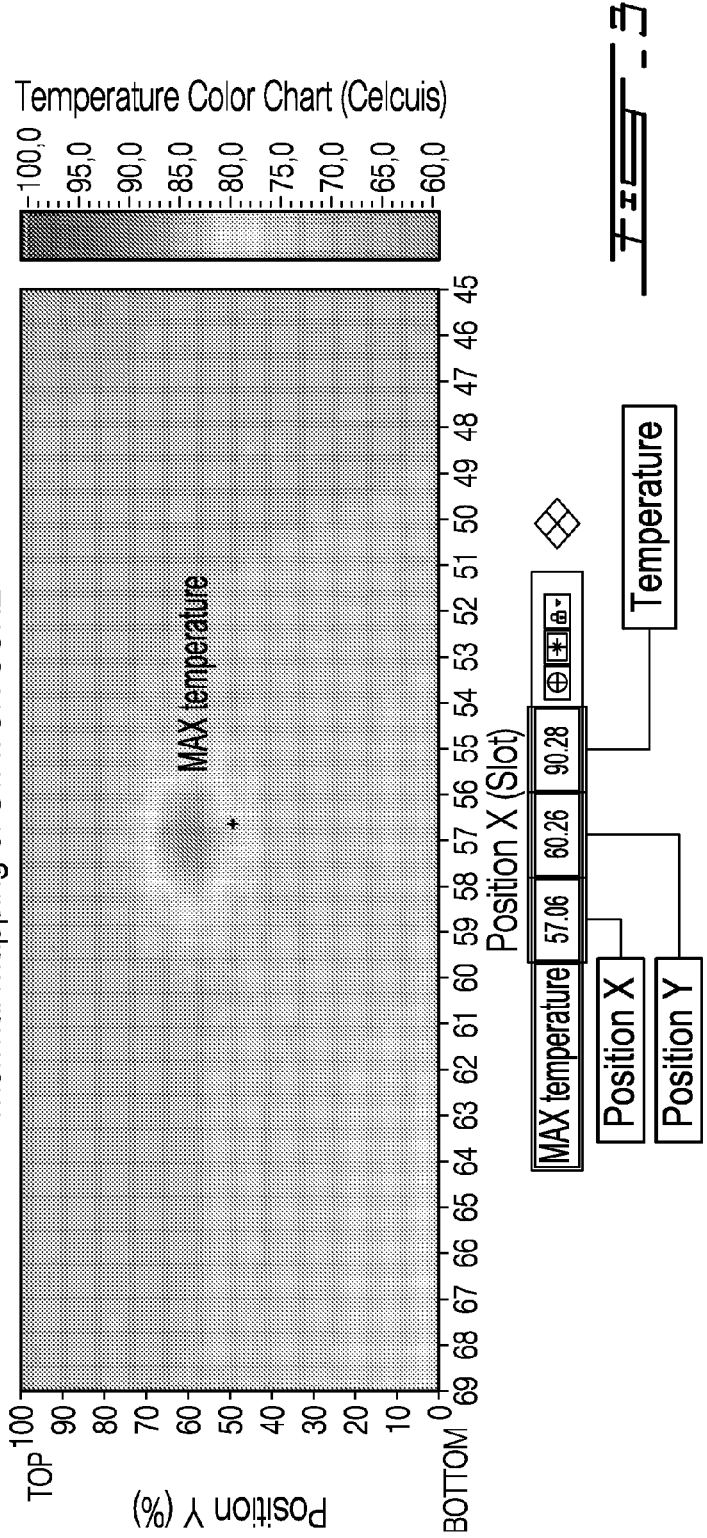
FIG. 3 is a screen shot of an interface to a system for temperature mapping according to the present invention.

Since the outer wall of the nucleus of the stator is accessible and because it consists of a highly heat conductive metal, the invention consists in placing, either during manufacture of the stator, or after its manufacture, at the location where it is used, as many heat probes as desired at predetermined locations and at acceptable costs. The easy accessibility of the outer wall permits to modify the stator in a few hours only and even without having to take the machine apart.

These predetermined locations will have to be in "heat correspondence" with the internal points that one wishes to thermally observe. In other words, the heat correction (or gradient) to be applied between an internal point of the stator for which there is a temperature probe, and the external point on which the external probe is applied, will be measured. For each temperature of the desired internal point, there is correspondence with a measurable temperature for an external corresponding point.

Knowing this temperature gradient, it is then possible to apply the same gradient in reverse manner for any external point of the stator on which there is disposed an external temperature probe, and to deduce the "real" temperature of the corresponding point or the corresponding internal zone of the stator.

If a deposit is accumulated on the internal walls of a cavity of a stator bar or if some other type of obstruction takes place, the probes that are installed at the extremities of the stator bars will detect a temperature increase when the machine is in operation, as well as the exact location of the problem.

A corrective measure, when a temperature increase of a stator bar is detected, consists of injecting a solvent in order to dissolve the deposits. The efficiency of the solvent can thereafter be ensured by checking whether the temperature of the stator bar returns to a normal level.

If the insulation of a stator bar becomes deteriorated, the probe that is installed at the extremity of the stator bar will detect an increase of temperature.

After having detected the problem, it is possible to determine the necessary corrective measures and to prevent damages to the machine. Following these corrective measures, efficiency of the corrective measure can be ascertained by checking that the temperature of the stator bar is uniform at all points.

With the proposed system, now that the limit of the number of probes has reached many hundreds, even a few thousands, the installation of a probe on each of the connections makes it possible to detect the quality of the welding points in each of the stator bars.

If one of the connection points becomes deteriorated, the probe that is installed on (or near) a connection point will detect a temperature increase.

After having detected the problem, corrective measures should be carried out to prevent damages to the machine. Following these corrective measures, it is possible to make sure that the corrective measures are efficient by verifying that the temperature of this connection point is normal.

Figure 4:
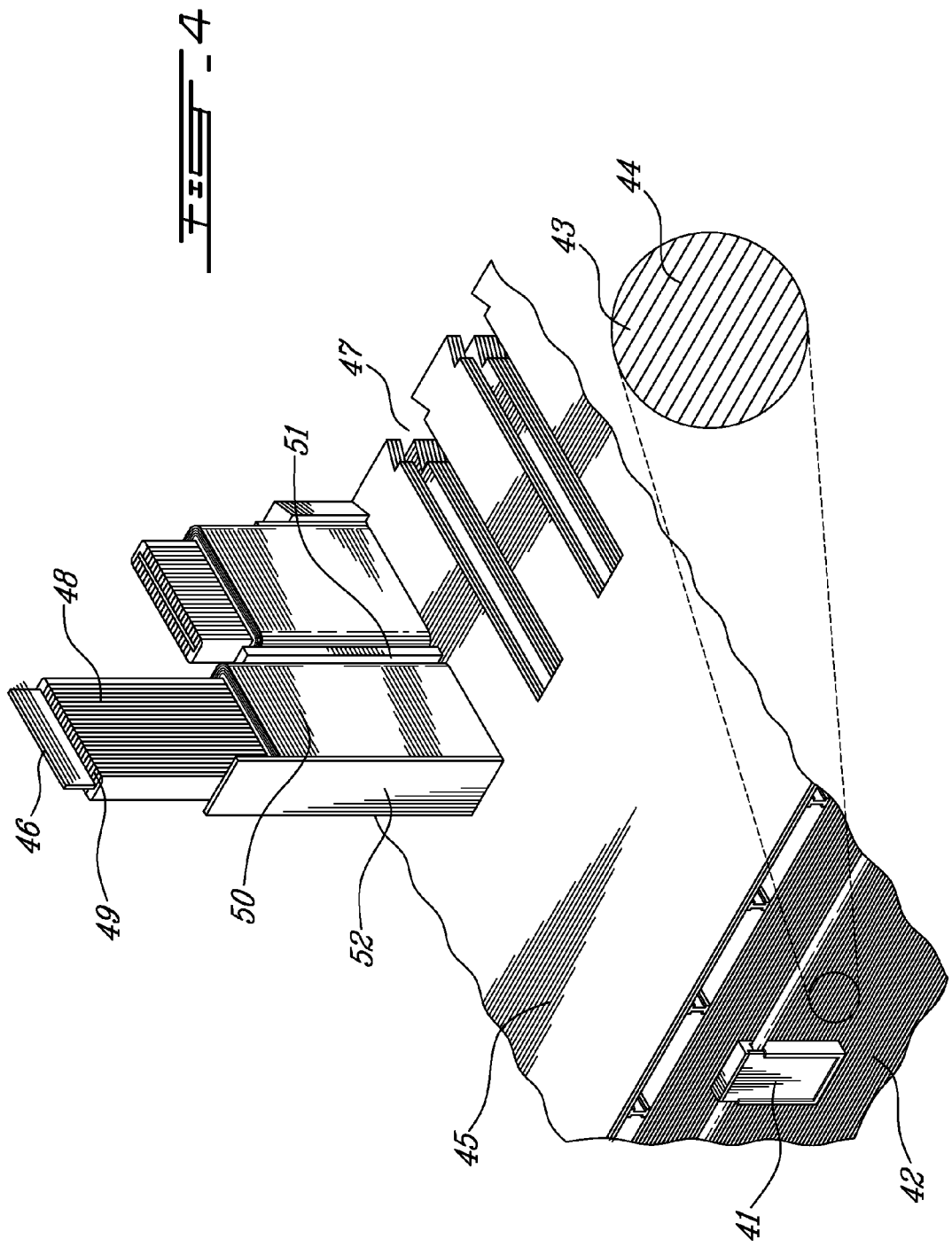
FIG. 4 is a schematic illustration showing localization of the internal probes and the external probes in and on the stator, according to a preferred embodiment of the present invention.

With respect to FIG. 4, it then becomes conceivable to install probes 41 on the external stator wall 42 of the stator nucleus, which comprises magnetic iron sheets 43 separated by isolators 44, in order to constitute a matrix along the entire length of the stator. With such an assembly, it is possible to take a measurement of the temperature at a multitude of points of a surface, which permits to detect and localize undesirable losses by Foucault currents when the machine is in operation.

If the insulation is dilapidated, the Foucault currents will intensify and local temperature will increase. The probes installed on this part of the stator will detect a temperature increase. Moreover, the interpolation algorithm identifies the location where the temperature is the highest, which is an indication of a loss of insulation. Inside the nucleus 45, stator bars 46 are fitted into stator slots 47, the stator bars 46 having multiple copper conductor strands 48 insulated by isolators 49, the assembled bar 46 being further insulated by a resin impregnated fabric 50 wound around the bar 46. Semi-conductive material 50 is wound around the assembled stator bar for heat transfer and grounding purposes. Internal probe 51 is inserted between the cartridges to permit the measure of the temperature gradient with probe 41.

The principle is based on the input and analysis by a computer program for acquisition and processing of a reconstituted signal originating from a group of temperature sensors that are connected in series. In a preferred embodiment of the present invention, all the temperature sensor probes are connected in series on a same pair of wires, to which a third wire is added for power supply. The 3-wire cable has a power supply line, a ground line and a data communication line. Connection of the temperature sensor probes in series makes it possible to install about a hundred sensors on the interior or exterior wall of the nucleus of the stator, to build a matrix of points distributed all around this nucleus.

One of the extremities of the series of sensors is connected to an acquisition device that permits reading of the temperature of each of the sensors of the matrix. A configuration and acquisition computer program makes it possible to localize the physical site of each of the sensors and to read their temperatures. Different treatments of these temperatures allow for a variety of analyses. It is for example possible to obtain a thermal mapping of the wall of the stator at various times and under various conditions of a machine by extrapolating the temperatures of the spaces between the measurement points.

The result of this mapping will allow the user to localize the hot points of the stator wall caused by a short circuit between the laminations, which are the signs of a problem of loss of insulation that can possibly lead to a major break. An early detection of this type of problem will permit to bring about corrective measures before more important damages are caused to the machine. Following the application of these corrective measures, it will be additionally possible to ensure the efficiency of the corrective measures by verifying that the temperature of the stator wall has return to uniform condition throughout the entire points.

The principles of measurement of the temperature gradient and measurement of the temperature of stator bars will first be described.

In order to measure the temperature gradient G, temperature should be measured at two distinct measuring points, i.e.:

$Tb(x, t1)$: temperature measurement of an internal probe located on the insulating layer of the stator bar (x) at a given time (t1) and $Ts(x, t1)$: temperature measurement of an external probe located on the external wall of the stator and opposite the notch of the stator bar (x) at a given time (t1)

The gradient (G) is then calculated in the following manner:

$$G = Tb(x,t1) - Ts(x,t1).$$

Moreover, when measuring $Tb(x, t1)$ and $Ts(x, t1)$, the generated heating load $P(t1)$ should be known. The heating load measurement will allow to deduce the temperature of each of the stator bars $Tb(x, t)$ by means of the external probes and at any given time (t) and under any given heating load $P(t)$:

$$Tb(x,t) = Ts(x,t) + (G \times P(t)/P(t1))$$

The features and advantages of the present invention will become better understood from the description of the following exemplary embodiments.

In a first exemplary embodiment and with respect to FIG. 5, the detection of defects in cooling ducts using the temperature measurement method of the present invention will be described.

A complete or even partial obstruction of the cooling ducts of the stator bars results in a loss of efficiency of the cooling system, thus producing a temperature rise of the stator bar.

The system and method of the present invention allow to detect a temperature increase of a defective bar. This rise would normally increase over time and would be present along the entire length of the bar.

Two external probes are installed on each of the bars, one of them being located in the top part of the stator nucleus and the other one being located in the bottom part of the stator nucleus. A temperature increase of the external probes of a bar (x) with respect to the other bars means that there is a defect in the cooling ducts.

The mapping of such a problem reveals a warmer zone along the entire length of the defective bar. This zone becomes increasingly hot as time goes by, as the obstructing deposits are accumulated and cause the ducts to be less and less efficient.

Figure 5:
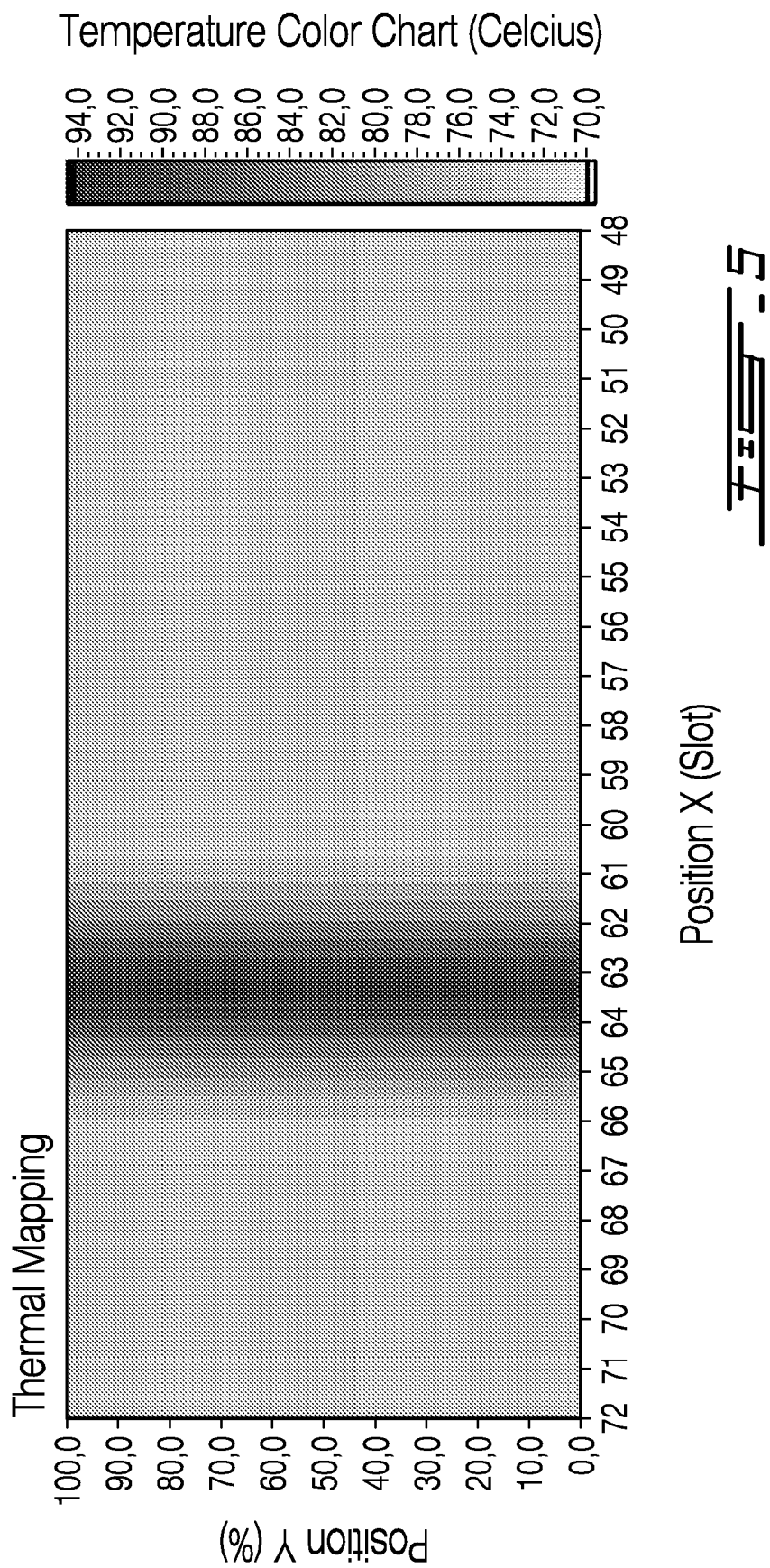
FIG. 5 is a temperature mapping for detection of defects in cooling ducts, in which position Y (%) refers to the height of the stator wall and position X (slot) refers to the slot number.
Figure 6:
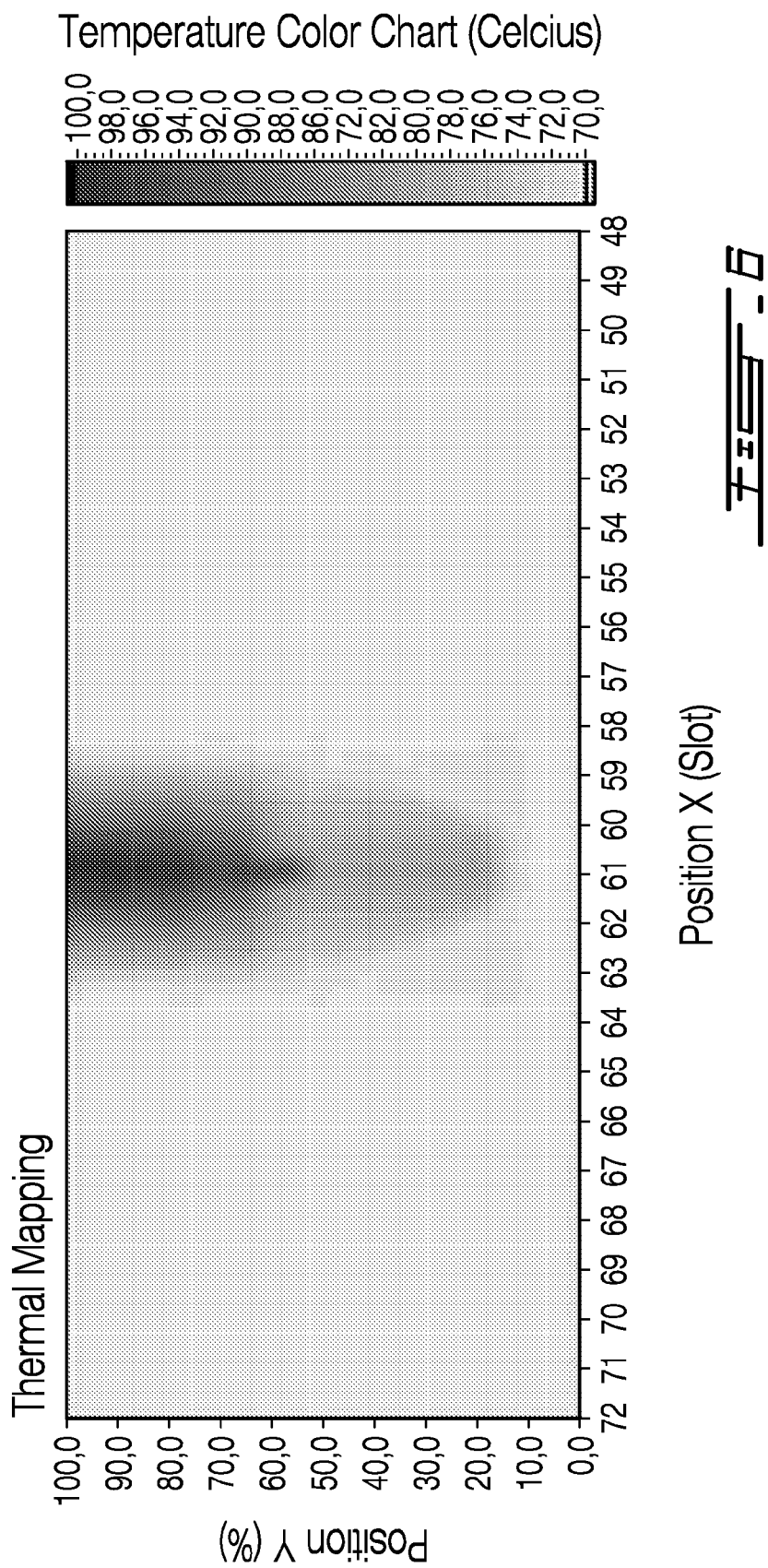
FIG. 6 is a temperature mapping for detection of loss of insulation between conductors, in which position Y (%) refers to the height of the stator wall and position X (slot) refers to the slot number.
Figure 7:
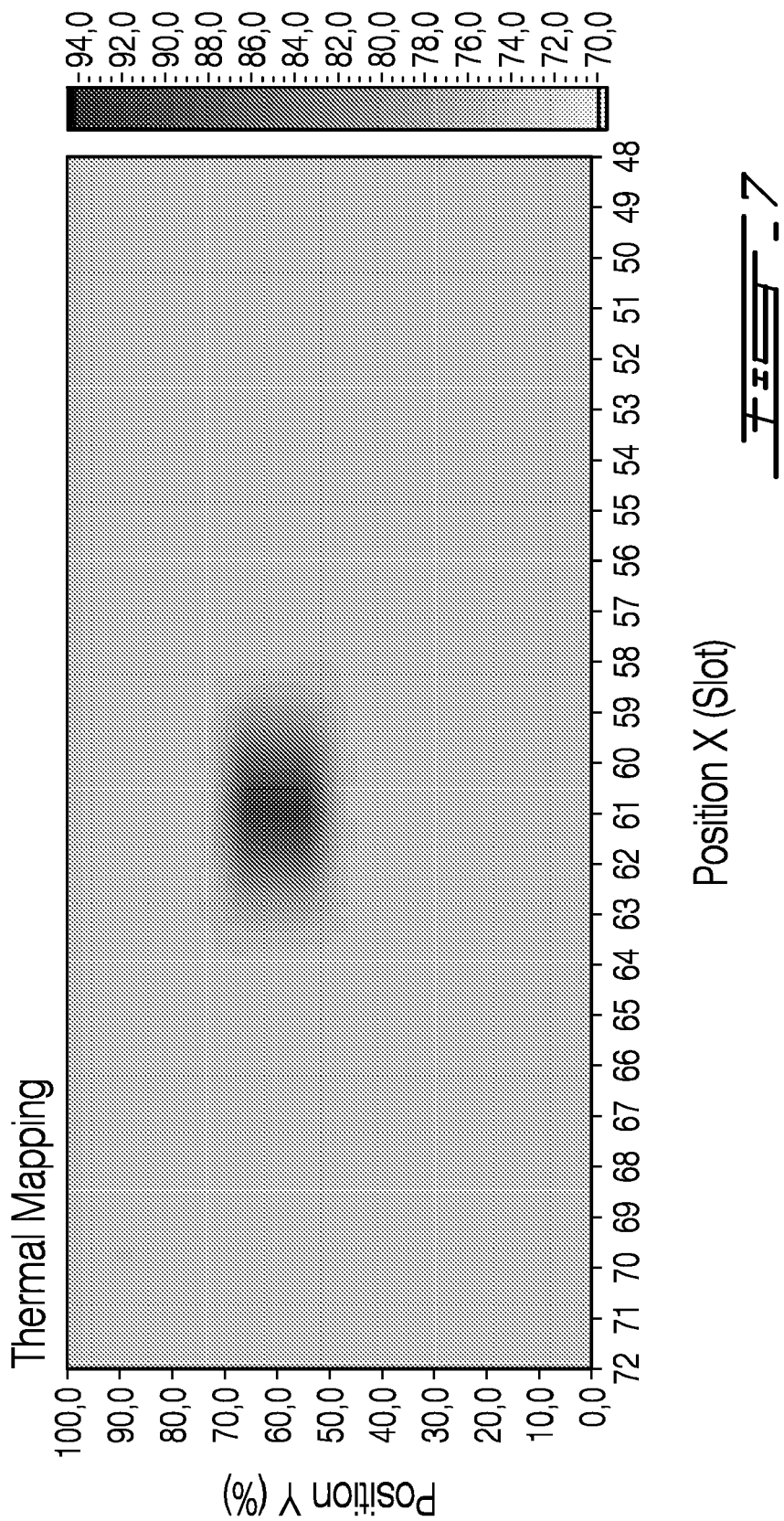
FIG. 7 is a temperature mapping for the detection of the loss of quality of the connections of the stator bars, in which position Y (%) refers to the height of the stator wall and position X (slot) refers to the slot number.

FIGS. 5, 6 and 7 are temperature mappings for the different examples in which:

position Y (%): means the height of the stator wall, given that 0%=bottom part of the wall, 100%=upper part of the wall;

position X (slot): is the slot number. In each machine, there are many slots (for the stator bars) and each of them is numbered from 1 to xxx.

temperature color chart: color scheme vs temperature

Now, with respect to FIG. 6, an example of detection of loss of insulation between conductors will be described. The loss of insulation between conductors is usually restricted to the mechanical stress zone of the bar, i.e. at the junction where the bar penetrates into the stator nucleus.

Therefore the problem may be detected before the damage becomes major. A problem of this nature is shown on the thermal map as a warmer zone, at either end of the bar, which becomes decreasingly warm towards the other end.

Now, with respect to FIG. 7, the detection of the loss of quality of the connections of the stator bars will be described. The connections of the stator bars are generally welded joints. When subject to mechanical, electrical, chemical and thermal stresses, these joints are deteriorated and may become resistive, thereby causing a local temperature increase. With this invention, the temperature of each of these connections may be measured.

Now, still with respect to FIG. 7, the detection of the loss of insulation of the stator laminations will be described. In order to detect a loss of insulation of the stator laminations, an important quantity of external probes must be installed at predetermined locations. A loss of stator insulation thermally causes a warmer zone.

With this invention and by means of a thermal mapping of the internal stator wall, it becomes easy to detect and localize the loss of insulation.

Figure 8:
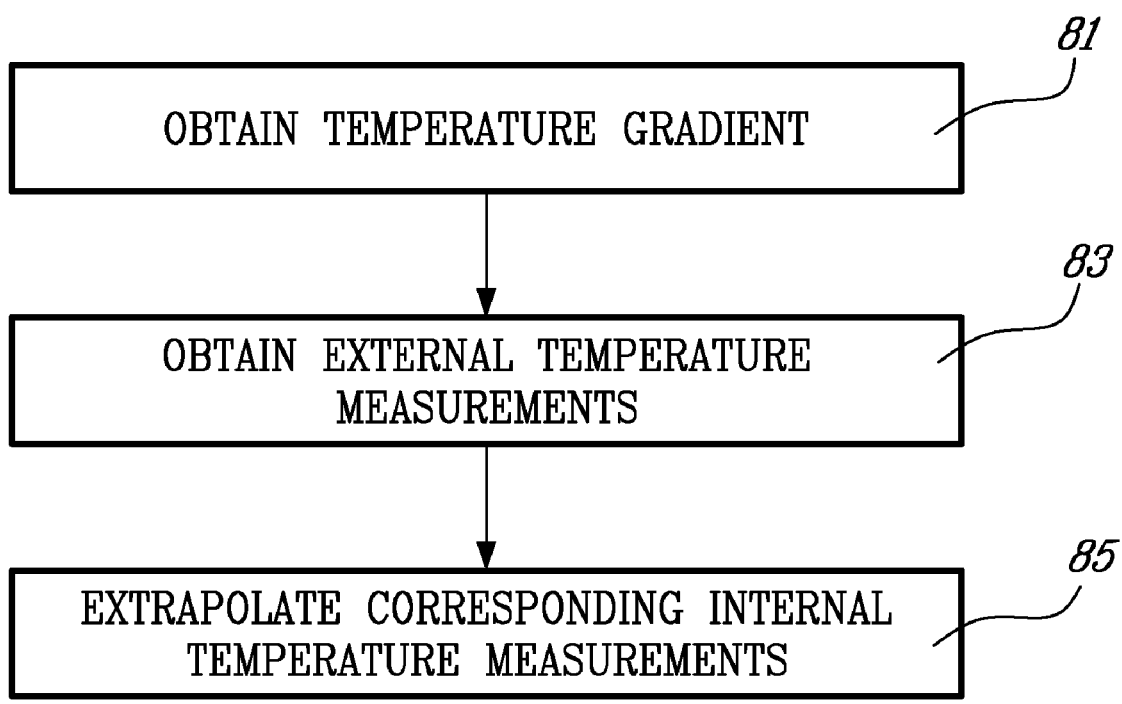
FIG. 8 is a flow chart of a method for non-intrusive determination of an internal temperature of a given area of an electrical machine stator according to the present invention.

With respect to FIG. 8, a method for non-intrusive determination of an internal temperature of a given area of an electrical machine stator will be described. In a first step 81, a temperature gradient between an internal wall of the stator and an external wall of the stator is obtained. In a second step 83, temperature measurements at locations on said external wall of said stator are obtained. In a last step 85, the temperature gradient and the external temperature measurements are used to extrapolate corresponding internal temperatures of the stator.

In additional steps, position data regarding the temperature probes and the extrapolated internal temperature values may be used to produce a thermal map of the stator. Position data regarding the temperature probes may be received from a network communication address for each of the external temperature probes. A mapping table or other correspondence relationship between the network address and the probe position may be used to determine the probe position, for each of the external temperature probes.

Now, with respect to FIG. 9, a system for non-intrusive determination of the internal temperature of a given area of an electrical machine stator will be described. A plurality of temperature probes 91a, 91b, 91c, 91d are shown to be installed on an external wall of said electrical machine stator for measuring an external temperature thereof. In a preferred embodiment of the present invention the probes 91 are connected in series and are in communication with a processing unit 93. The processing unit includes a communication module 95 for receiving temperature data from the probes 91. The communication module 95 may also receive other data, such as probe address and/or probe position data associated with the temperature measurements.

The processing unit 93 also includes a memory module 97 for storing a temperature gradient between the internal wall of the stator and the external wall of the stator. In one embodiment of the present invention, the temperature gradient may be pre-calculated and then loaded into the memory module 97 through a data communication link. In other embodiments, the temperature gradient may be calculated from internal and external temperature measurements gathered with the probes 91 and then stored in the memory module 97. The memory module 97 may also contain other data, such as a normal temperature range, which may be used by the processing unit 93 in order to check the operation of the stator.

The analysis module 99 of the processing unit 93 receives external temperature data and parameters stored in the memory module 97 and uses them to calculate internal temperature data. The analysis module 99 further uses the internal temperature data to provide, for example, corrective measures on the basis of measured temperature variations with respect to a normal temperature range. A control unit 101 in communication with the stator, receives corrective measures from the processing unit 93. The control unit 101 may also communicate with an alarm generating unit 103 responsive to control reports of the control unit 101.

In one embodiment of the present invention, the processing unit 93 may also include a video rendering module (not shown) for creating a thermal map from internal temperature data and temperature probe position data. In this case, as an alternative embodiment, the memory module 97 may store an address-position map allowing to calculate probe position data from probe address data and the address-position map. Additionally, the system may comprise a display unit 105 for displaying the thermal map generated by the processing unit 93.

It will be understood that numerous modifications thereto will appear to those skilled in the art. Accordingly, the above description and accompanying drawings should be taken as illustrative of the invention and not in a limiting sense. It will further be understood that the description is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

We claim:

1. A method for non-intrusive determination of an internal temperature of a given area of an electrical machine stator, comprising:
   obtaining a temperature gradient between an internal wall of said stator and an external wall of said stator;
   obtaining temperature measurements at locations on said external wall of said stator; and
   using said temperature gradient and said external temperature measurements to extrapolate corresponding internal temperatures of said stator.

2. A method as claimed in claim 1, further comprising:
   providing a set of normal internal temperatures for said electrical machine stator;
   comparing said extrapolated internal temperatures with said set of normal internal temperatures in order to determine a deviation therefrom;
   providing a corrective measure to said electrical machine stator if a deviation is detected.

3. A method as claimed in claim 2, further comprising:
   activating an alarm upon detecting a deviation.

4. A method as claimed in claim 1, wherein said obtaining a temperature gradient comprises the steps of:
   installing temperature measuring probes at a plurality of locations on said internal wall of said stator and obtaining internal temperature measurements;
   installing temperature measuring probes at a plurality of locations on said external wall of said stator, corresponding to said internal locations and obtaining external temperature measurements;
   using said internal and external temperature measurements to calculate said temperature gradient.

5. A method as claimed in claim 1, wherein said obtaining temperature measurements at external locations of said stator comprises:
   providing temperature probes at external locations of said stator;
   measuring temperature at said external locations; and
   providing position data of said probe external locations and said temperature measurements.

6. A method as claimed in claim 5, further comprising:
   using said position data and said extrapolated internal temperature values to produce a thermal map of said stator; and
   displaying said thermal map.

7. A method as claimed in claim 5, wherein said receiving probe position data comprises:

receiving a network communication address for each of said external temperature probes;

receiving a correspondence between said network address and said probe position; and determining said probe position using said correspondence and said network communication address for each of said external temperature probes.

8. A system for non-intrusive determination of the internal temperature of a given area of an electrical machine stator, comprising:

a plurality of temperature probes to be installed on an external wall of said electrical machine stator for measuring an external temperature thereof;

a processing unit having:
  a memory unit for storing a gradient temperature;
  an analysis module for receiving said external temperature data and calculating, using said temperature gradient, said internal temperatures; and
  a communication module for receiving said external temperature data from said plurality of temperature probes.

9. A system as claimed in claim 8, wherein said temperature probes are connected through a serial link to said communication module.

10. A system as claimed in claim 8, wherein said analysis module comprises a video rendering module for creating a thermal map from said internal temperature data and said probe position data and further comprising a display unit for displaying said thermal map.

11. A system as claimed in claim 10, wherein said memory unit further comprises an address-position map and wherein said probe position data is determined from said address data and said map.

12. A system as claimed in claim 8, wherein said analysis module provides corrective measures on the basis of temperature variations with respect to normal operating temperatures and further comprising a control unit receiving said corrective measures and controlling an operation of said stator.

13. A system as claimed in claim 12, further comprising an alarm generating unit responsive to control reports of said control unit.

\* \* \* \* \*